United States Patent [19]

Saussine et al.

[11] Patent Number: 4,659,829

[45] Date of Patent: Apr. 21, 1987

[54] METAL PEROXIDE COMPLEXES, THEIR MANUFACTURE AND USE FOR OXIDIZING HYDROCARBONS TO ALCOHOLS AND/OR KETONES

[75] Inventors: Lucien Saussine, Chatou; Alain Robine; Hubert Mimoun, both of Rueil-Malmaison, all of France

[73] Assignee: Institut Francais du Petrole, Rueil-Malmaison, France

[21] Appl. No.: 696,835

[22] Filed: Jan. 31, 1985

[30] Foreign Application Priority Data

Jan. 31, 1984 [FR]  France ............................ 84 01587
Feb. 2, 1984 [FR]  France ............................ 84 01736

[51] Int. Cl.$^4$ ............... C07D 401/14; B01J 31/22; C07B 41/02; C07B 41/06
[52] U.S. Cl. ............................. 546/2; 546/10; 546/12; 568/311; 568/342; 568/360; 568/385; 568/571; 568/832; 568/836; 568/910
[58] Field of Search ............................. 546/2, 10, 12

[56] References Cited

PUBLICATIONS

"Handbook of Chemistry & Physics (CRC)", pp. 392–393.

*Primary Examiner*—Mark L. Berch
*Attorney, Agent, or Firm*—Millen & White

[57] ABSTRACT

The invention concerns peroxide complexes of metals complying with the general formula LnMXpY, wherein M is a metal selected from groups VIII, IB and VIIB, particularly cobalt, X is an anionic group, for example carboxylate, R is an alkyl, cycloalkyl or arylalkyl group, n=1 or 2, p=0 or 1 and n+p=2.

L is a tridentated ligand from the group of 1,3 bis (2-pyridylimino) isoindolines.

These complexes are obtained by reaction of a hydroperoxide ROOH with a complex of formula LnMXp. They can be used in oxidizing hydrocarbons to a mixture of alcohols and ketones, either as reactants or as catalysts.

They are particularly useful to prepare tert-butanol by oxidation of isobutane in liquid phase, by means of an oxygen-containing gas such as air.

8 Claims, No Drawings

METAL PEROXIDE COMPLEXES, THEIR MANUFACTURE AND USE FOR OXIDIZING HYDROCARBONS TO ALCOHOLS AND/OR KETONES

The present invention concerns new peroxide complexes of a metal, complying with the general formula:

[I]LnMXpY wherein Y is a peroxo group or a group of formula OOR in which R is an alkyl or aralkyl group, L is a ligand as hereinafter defined, M is a metal, X is an anionic group, $n=1$ or 2, $p=0$ or 1 and $n+p=2$, as well as the use of these complexes as oxidation reactants or as catalysts for oxidizing hydrocarbons by means of oxygen, a peroxide or hydroperoxide, and particularly an organic hydroperoxide.

The peroxide complexes may particularly catalyze the hydroxylation of a hydrocarbon R'H by a hydroperoxide R"OOH.

Groups R' and R" are identical or different from radical R and selected from alkyl, cycloalkyl, aralkyl, alkenyl, cycloalkenyl and aralkenyl groups.

In the above-mentioned complexes, L is a tridentated chelating ligand of general formula (A), arbitrarily represented by BpI when $R_1$ to $R_{12}$ are each a hydrogen atom.

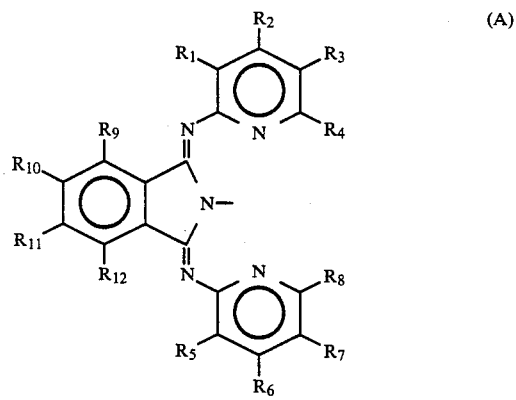

(A)

In this formula (A), each of symbols $R_1$ to $R_{12}$, separately represent, independently from one another, a hydrogen atom, an alkyl group of $C_1$ to $C_{12}$ carbon atoms for example, an aryl group of $C_6$ to $C_{14}$ carbon atoms for example, an aralkyl group of $C_7$ to $C_{30}$ carbon atoms for example, an alkoxy group of $C_1$ to $C_{12}$ carbon atoms for example, an alkoxyalkyl group of $C_2$ to $C_{20}$ carbon atoms for example, a halogen atom (Cl, F, Br, I) or a nitro group ($-NO_2$).

Two adjacent groups $R_1$ to $R_{12}$ may form together an aromatic ring with the carbon atoms to which they are linked. When $n=2$, the two ligands L may be identical or different.

The preferred ligands L are those wherein each group $R_1$ to $R_{12}$ represents a hydrogen atom or wherein groups $R_2$ and $R_6$, identical or different, each represent a methyl or tert-butyl group and are preferably identical; group $R_{11}$ represents a methyl or tert-butyl group and groups $R_1$, $R_3$, $R_4$, $R_5$, $R_7$ to $R_{10}$ and $R_{12}$ each represent a hydrogen atom.

X is an anionic group selected from:

a carboxylate anion such as acetate, propionate, benzoate pivalate, stearate, 2-ethyl-hexanoate, octoate, naphthenate or a perfluoric carboxylate, for example trifluoroacetate, an anion of organic acid such for example as an alkylphosphate or an alkylsulfonate, a hydroxide, mu-oxide or mu-peroxide anion.

X is preferably a carboxylate group.

Y is a mu-peroxo, peroxo, alkylperoxo, or aralkylperoxo group of formula ROO, wherein R is an alkyl or aralkyl group.

Y is preferably an alkylperoxo or aralkylperoxo group, R is preferably a tertiary group such for example as a tertbutyl or cumyl (1-phenyl-1-methyl-ethyl) group.

M represents a metal selected from groups VIII, $I_B$ and $VII_B$ of the periodic classification of elements (Handbook of Chemistry and Physics 37$^{th}$ edition 1955-56, pages 392-393).

M is advantageously selected from the following metals: cobalt, iron, manganese and copper, preferably cobalt.

Examples of 1,3-bis(2'-pyridylimino)isoindoline ligands, hereinafter called (BpI)H, used for manufacturing complexes according to the invention, are:

1,3-bis(2'-pyridylimino)isoindoline: (BpI)H
1,3-bis(4'-methyl-2'-pyridylimino)isoindoline: (4'Me-BpI)H
1,3-bis(4't-butyl-2'-pyridylimino)isoindoline: (4'tBu-BpI)H
1,3-bis(5'-chloro-2'-pyridylimino)isoindoline: (5'Cl-BpI)H
5-t-butyl-1,3-bis(2'-pyridylimino)isoindoline: (5tBu-BpI)H
5-t-butyl-1,3-bis(4'-methyl-2'-pyridylimino)isoindoline: (5tBu-4'Me-BpI)H
5-t-butyl-1,3-bis(4'-t-butyl-2'-pyridylimino) isoindolene: (5tBu-4'tBu-BpI)H Particularly preferred complexes are those of formulas:

(BpI)Co(OAc)OOtBu
(BpI)Co(OBz)OOtBu
(BpI)Co(p-NO$_2$BzO)OOtBu
(4'Me-BpI)Co(OAc)OOtBu,    (4'Me-BpI)Co(OBz)OOtBu
(5'tBu-BpI)Co(OAc)OOtBu,    (5tBu-BpI)-Co(OBz)OOtBu
(5'Cl-BpI)Co(OAc)OOtBu
(BpI)Co(octoate)OOtBu
(BpI)Co(OAc)OO cumyl, (BpI)Co(OBz)OO cumyl
(BpI)Fe(OAc)OOtBu, (BpI)$_2$Fe(OOtBu)
(BpI)Mn(OAc)OOtBu,    (BpI)Mn(OBz)OOtBu,
(BpI)$_2$MnOOtBu, (4'Me-BpI)$_2$MnOOtBu wherein symbols BpI, 4'Me-BpI, 5'Cl-BpI, 5'tBu-BpI have the same meaning as above and symbols OAc, OBz, p-NO$_2$BzO respectively represent the acetate, benzoate and p-nitrobenzoate groups, Me and tBu representing respectively methyl and tert-butyl groups.

The manufacture of the complexes, which will be described more in detail in the examples, may be performed in different manners.

1,3-bis(2'-pyridylimino)isoindoline ligands may be prepared by the method described by W. O. SIEGL J. Org. Chem. 42 (11) 1872 (1977).

Complexes of transition metals in divalent state LMX and L$_2$M may be obtained according to different procedures described in W. O. SIEGL (above reference) and more recently by R. R. GAGNE et al, Inorg. Chem. 20 3260—7 (1981)—with some modifications according to the nature of the X group or of the substituents on ligand L.

The synthesis in a single step of complexes LMX may be performed by reaction of 2-aminopyridine with phthalonitrile in the presence of the transition metal salt $MX_2nH_2O$. The product is generally obtained as precipitate and a purification is necessary to remove the phthalocyanine complex of low solubility which is formed in small amount. For LCo(OAc) complexes, the precipitate may be, for example, dissolved in acetic acid, filtered and the obtained filtrate evaporated under reduced pressure.

The alkylperoxo complexes, for example of cobalt (III), of general formula LCoX(OOR), may be easily prepared by addition of a hydroperoxide to a suspension of LCoX complex in a solvent of relatively low polar character such as dichloromethane, at a temperature from about $-40°$ to $+80°$ C., preferably from $-15°$ to $+40°$ C.; a quick solubilization takes place together with an intensified red color.

LCoX(OOR) complexes are then obtained easily by concentration of the solution.

This transformation may be performed in most of the usual solvents which do not react with hydroperoxides, such for example and by way of non limitative examples: benzene, chlorobenzene, 1,2-dichloro-ethane.

Sufficiently stable complexes may be isolated in pure state and kept in a refrigerator for several weeks.

One of the advantages of the LnMXpY complexes of the invention is that generally they are much more soluble than the divalent complexes LMX or $L_2$ M.

One of the most remarkable properties of the complexes of the invention is that they can stoichiometrically transfer oxygen to a hydrocarbon substrate such as an olefin, a saturated aliphatic hydrocarbon or an aromatic hydrocarbon.

These complexes have the property to stoichiometrically oxidize linear or branched alkanes to a mixture of alcohols and ketones. Tertiary alcohols are thus mainly obtained from branched alkanes.

Olefins are mainly hydroxylated in allyl position. Alkyl or cyclo-alkyl aromatic hydrocarbons are oxidized in benzyl position, essentially to a mixture of alcohol and ketone.

The ratio by weight of the substrate to be oxidized to the complex is generally from 1:1 to 500:1, preferably from 10:1 to 250:1.

The reaction temperature is about $0°$ C.$-180°$ C., preferably $20°-100°$ C.

Generally, the reaction is conducted under nitrogen atmosphere, the total pressure depending on the nature of the substrate and of the solvent and on the selected temperature.

According to another characteristic property, these complexes can be regenerated from corresponding reduced forms thereof by oxidation with an oxidant and may thus be used as oxidation catalysts.

It is thus possible to catalytically oxidize:
A cyclic or polycyclic, liquid or gaseous linear or branched alkane, preferably containing 2-20 carbon atoms, for example isobutane, isopentane, butane, hexane, octane.
A linear or cyclic olefin, optionally branched or comprising another group such for example as a ketone group, conjugated or not with the double bond, for example propene, butenes, cyclohexene, 1-methylcyclohexene, alpha and beta pinene.

An alkyl or cycloalkyl aromatic hydrocarbon having optionally one or more other substituents on the aromatic ring, for example ethylbenzene, toluene and tetralin.

The catalysts according to the invention are particularly well adapted for the conversion of isoparaffins to tertiary alcohols.

In particular, it is well known in the prior art that isobutane may be thermally oxidized in the absence or the presence of a catalyst to prepare a tert-butanol and hydroperoxide mixture also containing acetone, methanol and ditert-butyl peroxide tBuOOtBu, as described for example in: J. K. KOCHI and R. A. SHELDON ch. II—metal catalyzed oxidations of organic compounds. Academic press (1981).

D. E. WINKLER et al—U.S. Pat. No. 2,845,461 (1958) have disclosed conditions for obtaining a good ratio of hydroperoxide to tert-butanol.

BJ. BARONE et al—U.S. Pat. No. 3,974,228 (1976) use lanthanum oxide to increase the selectivity to hydroperoxide during the oxidation of tertiary alkanes.

A. M. BROWNSTEIN et al—U.S. Pat. No. 4,028,423 (1977) obtain a good selectivity to hydroperoxide by catalyzing the oxidation of isobutane by copper polyphthalocyanine activated with an aromatic amine.

Recent patents to EG. FOSTER et al—EP No. 76,532, EP No. 76,533 and EP No. 76,534 (1983)—disclose an improvement in the tert-butyl hydroperoxide production, while maintaining a good selectivity for low isobutane conversions, by proceeding above the critical temperature and pressure.

It is known that the oxidation of isobutane in the presence of cobalt soluble salts (cobalt (II) octoate or naphthenate) is more rapid than the oxidation without catalyst and gives mainly tert-butanol.

D. E. WINKLER and G. W. HEARNE (Ind. Eng. Chem. 53, (1961), 655-8) have shown, in this occurrence, the increased formation of split-off products (acetone, methanol, acids). The total yield of tert-butyl peroxide and tert-butanol is decreased by about 10% as compared to the yield obtained by oxidation without catalyst.

B. E. JOHNSTON and al, in U.S. Pat. No. 3,825,605 (1974), use a solid catalyst consisting of a molybdenum or tungsten oxide also containing other metals (Fe, Co, Cr, Al) in small proportion.

R. H. WILLIAMS et al, in U.S. Pat. No. 3,816,548 (1974), use phthalocyanine of various metals (Mn, Fe, Co, Cu) to oxidize isoparaffins, mainly to tertiary alcohols.

Phthalocyanines of different transition metals are well known to decompose the intermediary hydroperoxides obtained by oxidation of such hydrocarbons as cyclohexene, ethylbenzene and cumene.

Complexes of transition metals having a structure related to the phthalocyanines have been claimed as catalysts for decomposing cyclohexyl hydroperoxide to cyclohexanol and cyclohexanone in the presence of cyclohexane; J. D. DRULINER et al, U.S. Pat. No. 4,326,084 (1982), corresponding to the European application EP No. 27,937 (1981).

H. R. GRANE et al, in U.S. Pat. No. 4,294,999 (1981) and U.S. Pat. No. 4,296,262 (1981), oxidize isobutane in the presence of a molybdenum soluble salt so as to obtain a mixture containing about 3 times more tert-butanol content than hydroperoxide. They decompose the hydroperoxide by thermal treatment and thus obtain an effluent containing 80% tert-butanol, 10% acetone and 5.5% methanol, by weight, with respect to the total effluent weight.

These authors have also claimed, in U.S. Pat. No. 4,296,263 (1981), an extended use of this method for oxidizing mixtures of isobutane and n-butane in the presence of soluble salts of various metals (Cr, Co, Ni, Mn), the operating conditions being such as to minimize the oxidation of n-butane. Acetone, methanol and other oxygenated by-products co-distill with tert-butanol and are found in the final product.

R. T. ADAMS et al, in U.S. Pat. No. 3,829,510 (1974), oxidize isobutane to acetic acid in the presence of a catalyst selected from the salts of various metals (Co, Cu, Mn ...) with a recycling of methyl acetate and hydrogenation of the mixture tert-butanol, acetone, methanol, methyl acetate, to convert acetone to isopropyl alcohol and obtain a mixture useful as motor fuel constituent.

The use of catalysts for oxidizing isoparaffins gives oxidates of high tertiary alcohols content but not free of hydroperoxides and of by-products. For the direct production of tert-butanol, it is important to obtain a maximum value of the ratio of tert-butanol to tert-butyl hydroperoxide, while maintaining a good yield. This is the more important as a thermal decomposition of tert-butyl hydroperoxides, studied by N. A. MILAS and M. SURGENOR J. Am. Chem. Soc. 68 205 (1946), does not yield more than 85% tert-butanol, whereas the thermal decomposition of ditert-butyl peroxide gives mainly acetone.

The use as catalysts of the new complexes according to the invention provides for the oxidation of isobutane by oxygen of the air, in the presence of one of the above-defined complexes, to a mixture of tert-butanol and tert-butyl hydroperoxide of much higher tert-butanol content than the mixtures obtained according to the prior art.

The use of the complexes according to the invention also makes possible to proceed at lower temperatures than those of the prior art, while maintaining a high reaction velocity, thereby decreasing the formation of by-products. The catalyst used in the process of the invention has the further advantage of a longer life time than that of soluble cobalt salts, for example octoate, used in the prior art.

The catalysts of the present invention may either directly intervene in the oxidation step, or in the decomposition of the hydroperoxide ROOH in presence of isoparaffin so as to obtain a larger alcohol amount.

A/ The oxidant is a hydroperoxide.

The reaction may be performed in absence or presence of such a solvent as, for example, benzene, 1,1,2-trichloro-2,2,1-trifluoroethane.

The catalyst amount ranges from 1 to $10^4$ ppm of complex in proportion of the substrate to be oxidized, preferably from 1 to 5000 ppm and more particularly 10–500 ppm.

The reaction temperature is from $-20°$ C. to $+180°$ C., preferably $0°-100°$ C.

The hydroperoxide is slowly added so that its concentration in the reaction medium is kept low, i.e. about 0.1–10% by weight in proportion to the weight of the reaction mixture, preferably 0.5–5%. It may be added either pure or in solution in the compound to be oxided or in another solvent.

B/ The oxidant is oxygen.

The hydrocarbon R′H being oxidized to hydroperoxide R′OOH in conventional conditions, the catalyst $L_nMX_pY$ has for object to decompose the hydroperoxide to alcohol while hydroxylating the hydrocarbon R′H, as shown by stoichiometrical tests in the examples.

The reaction temperature is about $40°-180°$ C., preferably about $80°-160°$ C. The reaction is preferably initiated by means of a free radicals initiator and advantageously by a peroxide or hydroperoxide at a concentration of 0.1–1% by weight with respect to the hydrocarbon; in a particularly advantageous embodiment, the hydrocarbon part of the peroxide or hydroperoxide has the same structure as the hydrocarbon to be oxidized.

When oxidizing isobutane, the reaction is conducted in liquid phase under a pressure generally from about 1 to 10 megapascals (MPa), preferably 2–6.5 MPa.

The reaction is preferably initiated by ditert-butyl peroxide or tert-butyl hydroperoxide at 0.1–1% by weight with respect to isobutane.

The oxygen partial pressure is generally about 0.05–0.5 MPa, preferably 0.15–0.4 MPa. The oxygen is either pure or diluted with an inert gas, e.g. nitrogen, or with a mixture of inert gases. Air, or air enriched with oxygen, or air diluted with an inert gas such as nitrogen, may also be used. Preferably air alone is used.

The amount by weight of catalyst ranges from about 1 to 5,000 ppm of complex with respect to the hydrocarbon to be oxidized, more particularly 10–500 ppm.

The catalyst may be introduced in totality at the beginning of the reaction or by small fractions during the whole reaction time.

The reaction may be conducted in a reactor of the continuous type or of the batch type.

The present invention is illustrated by the following nonlimitative examples:

EXAMPLE 1

Preparation of complex No 1 (BpI)Co(OAc)OOtBu 2 ml of tert-butyl hydroperoxide (tBuOOH) containing 20% of ditert-butyl peroxide (tBuOOtBu) are added, drop by drop, at $20°$ C., to 1 g of complex (BpI)-Co(OAc) (2.4 mmoles) suspended into dichloromethane.

After one hour of reaction at $20°$ C., the resultant red solution is dried over $Na_2SO_4$. After filtration and concentration under vacuum, the product is precipitated by addition of 10 ml of anhydrous ether. It is filtered and then washed 4 times with an ether-pentane mixture (½) at $0°$ C. and dried under vacuum over $P_2O_5$. 1 g of complex is recovered (molar yield of 82.5% with respect to the initial complex).

Infra-red analysis: (O—O) 880 cm$^{-1}$ (C—H)=2980 cm$^{-1}$

Nuclear magnetic resonance analysis in deuteriated dichloromethane: (NMR) delta (ppm): 0.47 (s, 9H); 1.64 (s, 3H) 7.1 to 8.2 (m, 10H); 8.9 (d, 2H).

Elementary analysis: $C_{24}H_{24}N_5O_4CO$

| Calculated for the formula: | C 57.04 | H 4.75 | N 13.86 | O 12.67 |
|---|---|---|---|---|
| Found: | C 57.13 | H 4.90 | N 13.77 | O 12.60 |

EXAMPLE 2

Preparation of complex No 2 (BpI)Co(OAc)OO cumyl.

The synthesis is conducted in the same operating manner as in example 1. 4.2 ml of 80% cumyl hydroperoxide are added at 0° C. (10 minutes) to a suspension of 2 g of (BpI)Co OAc complex (4.8 mmoles) in 50 ml of benzene. After 1 h 30 at 20° C., 0.6 g of (BpI)Co OAc complex (30%) is separated by filtration. The red solution gives, after a treatment identical to that of example 1, 1.65 g of brown crystals (60.5%). Infra-red analysis: (O-O)=840 cm$^{-1}$ NMR analysis: delta (ppm): 0.76 (s, 6H); 1.64 (s, 3H) 6.6–8.2 (m, 15H); 8.9 (d, 2H).

Elementary analysis: $C_{29}H_{26}N_5O_4Co$

| Calculated for the formula: | C 61.38 | H 4.58 | N 12.35 | O 11.29 |
|---|---|---|---|---|
| Found: | C 61.02 | H 4.70 | N 11.99 | O 11.24 |

EXAMPLE 3

Preparation of complex No 3 (BpI)Co(OBz)OOtBu 7.5 g (15.7 mmoles) of (BpI)Co OBz complex are suspended into dichloro-methane (150 ml) and treated at 20° C. with 10 ml of tert-butyl hydroperoxide at 80%. After 4 h of stirring at 20° C., the solubilization is practically complete. 0.4 g (5.3%) of the initial complex is separated by filtration. By treatment of the solution in the same manner as in example 1, 8.3 g of brown solid are obtained (93.3%).

Infra-red analysis: (O-O) 870 cm$^{-1}$, (C-H) 2980 cm$^{-1}$

NMR analysis: delta (ppm): 0.52 (s, 9H), 7–8.2 (m, 15H); 9 (d, 2H)

Elementary analysis: $C_{29}H_{26}N_5O_4Co$

| Calculated for the formula: | C 61.38 | H 4.58 | N 12.35 | O 11.29 |
|---|---|---|---|---|
| Found: | C 60.35 | H 4.51 | N 12.01 | O 11.2 |

EXAMPLE 4

Preparation of the complex No. 4 (BpI)Co(OBz)OO Cumyl 5 g (10.5 mmoles) of (BpI)CoOBz complex are treated at 20° C. with 6.5 ml of 80% cumyl hydroperoxide in 90 ml of dichloromethane for 7 hours, up to complete dissolution. After treatment, the product is obtained by crystallization at 0° C. in an ether-pentane mixture (1/1), after separation of a less soluble impurity (1.1 g). 3 g of product (45.5%) are obtained.

Infra-red analysis: (O-O) 880 cm$^{-1}$

NMR analysis: delta (ppm): 0.68 (s, 6H); 6.6–8.2 (m, 15H) 9.05 (d, 2H)

Elementary analysis: $C_{34}H_{28}N_5O_4Co$

| Calculated for the formula: | C 64.87 | H 4.45 | N 11.13 | O 10.17 |
|---|---|---|---|---|
| Found: | C 63.85 | H 4.28 | N 11.02 | O 10.07 |

EXAMPLE 5

Preparation of complex No 5 (BpI)Co(p-NO$_2$BzO)OOtBu 400 mg (0.76 mmoles) of (BPi)Co(p-NO$_2$BzO) complex, suspended into 10 ml of dichloromethane, are treated at 20° C. with 0.5 ml of 80% tBuOOH for 2 h. The resultant red solution is treated as in example 1 and gives 300 mg of complex (64%).

Infra-red analysis: (O-O) 850 cm$^{-1}$ (C-H) 2980 cm$^{-1}$

NMR analysis: delta (ppm): 0.57 (s, 9H); 7–8.6 (m, 14H) 8.9 (d, 2H)

Elementary analysis: $C_{29}H_{25}N_6O_6Co$

| Calculated for the formula: | C 56.87 | H 4.08 | N 13.72 | O 15.69 |
|---|---|---|---|---|
| Found: | C 56.14 | H 4.15 | N 13.55 | O 15.39 |

EXAMPLE 6

Preparation of complex No 6 (4'Me-BpI)Co(OAC)OOtBu. This complex is prepared at 0° C. from 3.55 g (8 mmoles) of (4'Me-Bpi)CoOAC complex suspended into 70 ml of dichloromethane and 6 ml of 80% tBuOOH. The solubilization is complete after 15 minutes. After 45 mn at 0° C., a treatment as in example 1 gives 4 g of brown precipitate (94%).

Infra-red analysis: (O-O) 878 cm$^{-1}$ (C-H) 2970 cm$^{-1}$

NMR analysis: delta (ppm): 0.5 (s, 9H); 1.64 (s, 3H); 2.58 (s, 6H); 6.9 to 8.2 (m, 8H); 8.7 (d, 2H)

Elementary analysis: $C_{26}N_{28}N_5O_4Co$

| Calculated for the formula: | C 58.54 | H 5.25 | N 13.13 | O 12.01 |
|---|---|---|---|---|
| Found: | C 58.27 | H 5.36 | N 13.11 | O 12.6 |

EXAMPLE 7

Preparation of complex No 7 (4'Me-BpI)Co(OBz)OOtBu. This complex is prepared at 0° C. from 2.1 g (4.15 mmoles) of (4'Me-BpI)CoOBz complex in 40 ml of dichloromethane and 3 ml of 80% tBuOOH. After 3 h at 0° C., the solubilization is almost complete and the undissolved starting product (150 mg, i.e. 7.1%) is separated by filtration. The treatment of the solution according to the procedure defined in example 1 gives 2.2 g of brown precipitate (89%).

Infra-red analysis: (O-O) 863 cm$^{-1}$ (C-H) 2975

NMR analysis: delta (ppm): 0.55 (s, 9H), 2.55 (s, 6H) 6.9 to 8.4 (m, 13H) 8.86 (d, 2H)

Elementary analysis: $C_{31}H_{30}N_5O_4Co$

| Calculated for the formula: | C 62.53 | H 5.04 | N 11.76 | O 10.75 |
|---|---|---|---|---|
| Found: | C 62.14 | H 5.10 | N 11.32 | O 11.07 |

EXAMPLES 8 to 19

Stoichiometrical oxidation of alkanes with peroxide complexes.

In a heat-insulated reactor, 1 mmole of complex is introduced into 25 ml of substrate to oxidize. The mixture is degased and heated under nitrogen atmosphere.

The products are titrated by vapor phase chromatography (VPC) with internal testing, after optional destruction of the unconverted complex by means of an excess of triphenyl phosphine.

The results are summarized in Table I. The yields are expressed in relation to the complex.

EXAMPLES 20 to 26

Hydroxylation of alkanes by hydroperoxides, catalyzed by peroxide complexes.

10 millimoles of hydroperoxide, either pure or as a solution, are progressively added, under nitrogen atmosphere, in ½ hour, to a solution of 0.01 millimole of catalyst into 25 ml of alkane to oxidize at 80° C. The mixture is stirred for 1 additional hour at 80° C. and analyzed by VPC.

The results are summarized in Table II. A very clear improvement of the yield of hydroxylation product is obtained as compared to the reference test (example 25) at equal cobalt concentration.

The yields are expressed with respect to the hydroperoxide.

EXAMPLE 27

0.1 mole of tert-butyl hydroperoxide, diluted into 10 ml of 1,1,2-trichlorotrifluoroethane, are progressively added, during 30 minutes, to 65 g of isobutane containing 100 ppm of (BpI)Co(OBz)OOtBu complex, maintained at 90° C. After a total reaction time of 90 minutes, the mixture is cooled and analyzed.

The iodometric determination shows the almost complete disappearance of the hydroperoxide (95%). The VPC determination shows the formation of 130% tert-butanol with respect to the hydroperoxide charge.

EXAMPLES 28 to 41

80 g of isobutane (1.38 mole) are introduced in an enamelled reactor.

The system is heated to the reaction temperature indicated in Table III. When the pressure is stable, 0.5 g of ditert-butyl peroxide (0.6% by weight with respect to isobutane involved) is added, as initiator, and catalyst in solution into 1 ml of tert-butanol.

The oxygen partial pressure is set at 0.4 MPa. The temperature and pressure are maintained constant by means of a thermal regulation device and oxygen addition.

At the end of the test, the mixture is cooled down to room temperature and degased. The hydroperoxide is titrated by iodometry; tert-butanol, acetone and methanol are titrated by vapor phase chromatography (VPC) after reduction of a test fraction with an excess of triphenylphosphine. Tert-butanol present before reduction is equal to the difference between total tert-butanol after reduction and tert-butyl hydroperoxide.

In examples 29 and 30, the whole catalyst is introduced at the beginning of the reaction. For example 31, the complex is introduced in two steps as a solution in tert-butanol, at the beginning and at the middle of the reaction time.

In tests 32 to 41, the catalyst is introduced, as a solution in tert-butanol, in several steps (every 30 mn for tests 32 to 35 and every 45 minutes for tests 36 to 41). Example 28 is a reference test; the oxidation takes place in absence of catalyst. Example 33 is a reference test in presence of cobalt octoate as catalyst. An increase of the velocity and selectivity to tert-butanol, as compared with the two reference tests, is observed.

The results are summarized in Table III.

The selectivity (S) is expressed in moles of each formed product with respect to the number of converted isobutane moles.

The selectivity (S) is given by the formula:

$$S = 100 \frac{\text{Number of moles formed product}}{\text{Number of moles converted isobutane}}$$

TABLE I

| EXAMPLES | COMPLEXES | Sustrate | T °C. | TIME min | Product(s) and molar yield(s) with respect to the complex in % |
|---|---|---|---|---|---|
| 8 | (BpI)Co(OAc)OOtBu | Cyclohexane | 80 | 75 | cyclohexanol (30) cyclohexanone (16) |
| 9 | (BpI)Co(OAc)OOcumyl | " | " | " | cyclohexanol (24) cyclohexanone (35) |
| 10 | (BpI)Co(OBz)OOtBu | " | " | " | cyclohexanol (10) cyclohexanone (24) |
| 11 | (4Me-BpI)Co(OAc)OOtBu | " | " | " | cyclohexanol (30) cyclohexanone (22) |
| 12 | (BpI)Co(OBz)OOtBu | cis-decaline | " | " | 9 cis-decalol (17) 9 trans-decalol (60) |
| 13 | (BpI)Co(OAc)OOtBu | octane | " | " | Octanol[a] (18,5) octanone[b] (38,0) |
| 14 | (BpI)Co(OAc)OOcumyl | isobutane | " | 60 | Tert-butanol (10) |
| 15 | (BpI)Co(OAc)OOtBu | Cyclohexene | 40 | 75 | 2-cyclohexene 1-ol (31) 2-cyclohexene 1-one (18) |
| 16 | (BpI)Co(OBz)OOtBu | " | " | 120 | 2-cyclohexene 1-ol (5) 2-cyclohexene 1-one (42) |
| 17 | (BpI)Co(OAc)OOtBu | Ethylbenzene | 45 | 90 | 1-phenyl-ethanol (3,5) acetophenone (40) |
| 18 | (BpI)Co(OBz)OOtBu | tetraline | 80 | 90 | alpha-tetralol (41) alpha-tetralone (33) |
| 19 | (4'Me-BpI)Co(OBz)OOtBu | cyclohexane | 80 | 75 | cyclohexanol (15) cyclohexanone (35) |

[a]octanol is a mixture of 1, 2, 3 and 4 octanols
[b]octanone is a mixture of 2, 3 and 4 octanones

TABLE II

| EXAMPLES | Catalyst | ppm/substrate Co. | ppm/substrate complex | Hydroperoxide | alkane | product(s) (molar yield %) | total yield in %[a] |
|---|---|---|---|---|---|---|---|
| 20 | (BpI)Co(OAc)OOtBu | 15 | 128 | t-butyl[b] | cyclohexane | cyclohexanol (28.5) cyclohexanone (16.5) | 61.5 |
| 21 | (4Me-BpI)Co(OAc)OOtBu | " | 135 | " | " | cyclohexanol (33) cyclohexanone (17) | 67 |
| 22 | (BpI)Co(OBz)OOtBu | " | 144 | " | " | cyclohexanol (29) cyclohexanone (15) | 59 |
| 23 | (BpI)Co(OAc)OOCumyl | " | 144 | cumyl[c] | " | cyclohexanol (39) cyclohexanone (17) | 73 |
| 24 | (BpI)Co(OAc)OOtBu | " | 128 | t-butyl[d] | " | cyclohexanol (31) cyclohexanone (22) | 75 |
| 25 | Co(oct)2 | " | | t-butyl[b] | " | cyclohexanol (11.5) cyclohexanone (8.5) | 28.5 |
| 26 | (BpI)Co(OAc)OOtBu | " | 128 | " | octane | octanol (8.9) octanone (9.9)[e] | 28.7 |

[a]The total yield is calculated on the assumption that the formation of one mole of ketone requires 2 moles of hydroperoxide
[b]98% pure tert-butyl hydroperoxide is used
[c]80% cumyl hydroperoxide in cumene is used
[d]Hydroperoxide is introduced as a solution in tert-butanol (50% by volume)
[e]Octanol is formed of a mixture of 1, 2, 3 and 4 octanols and octanone of a mixture of 2, 3 and 4 octanones.

TABLE III

| EX. | Catalyst | ppm/isobutane metal | ppm/isobutane complex | T °C. | Time min. | convers. % | SELECTIVITY (S) % tert-butanol | tert-butyl hydroperoxide | acetone | methanol | tert-butanol tert-butyl hydroperoxide |
|---|---|---|---|---|---|---|---|---|---|---|---|
| 28 |  | 0 | 0 | 125 | 300 | 10.5 | 32.2 | 59.5 | 5.4 | 1.5 | 0.54 |
| 29 | (BpI)Co(OBz)OOtBu | 10.4 | 100 | 125 | 23 | 5.3 | 73.4 | 9.2 | 5.3 | 5.8 | 7.97 |
| 30 | " | 10.4 | 100 | 100 | 110 | 5.5 | 79.1 | 9.8 | 2.4 | 2.5 | 8.07 |
| 31 | " | 20.8 | 200 | 110 | 310 | 16.5 | 85.6 | 9.3 | 6.4 | 3.9 | 9.2 |
| 32 | " | 8.3 | 80 | 120 | 120 | 12.8 | 74.8 | 10.1 | 6.1 | 4.8 | 7.4 |
| 33 | Co(oct)$_2$ | 8.3 | — | 120 | 120 | 7.2 | 64.5 | 25.5 | 2.6 | 2.3 | 2.53 |
| 34 | (BpI)Co(octoate)OOtBu | 8.3 | 83 | 120 | 120 | 13.4 | 74 | 10.3 | 6.4 | 5 | 7.18 |
| 35 | (BpI)Co(OAc)OOtBu | 8.3 | 71 | 120 | 120 | 11.5 | 76.5 | 10.2 | 5.3 | 4.2 | 7.5 |
| 36 | (BpI)Co(OAc)OOtBu | 8.3 | 71 | 110 | 180 | 12.2 | 82 | 9.2 | 6.1 | 3.9 | 8.9 |
| 37 | (BpI)Co(OBz)OOtBu | 8.3 | 80 | 110 | 180 | 12.7 | 83.5 | 8.2 | 6.4 | 4.2 | 10.2 |
| 38 | (4'Me-BpI)Co(OAc)OOtBu | 8.3 | 75 | 110 | 180 | 11.8 | 81.8 | 8.6 | 5.3 | 3.9 | 9.5 |
| 39 | (BpI)Co(OAc)OOtBu | 8.3 | 71 | 110 | 180 | 12 | 83 | 10.5 | 5.5 | 3.9 | 7.9 |
| 40 | (BpI)Co(OBz)OOtBu | 16.6 | 160 | 110 | 420 | 24 | 82.5 | 7.3 | 7.4 | 3.9 | 11.2 |
| 41 | (BpI)Co(OBz)OOtBu | 10 | 96 | 120 | 240 | 21 | 80 | 8.8 | 8.2 | 5 | 9.1 |

What is claimed as the invention is:

1. Metal peroxide complexes of the general formula LnMXpY wherein L is a ligand of formula (A),

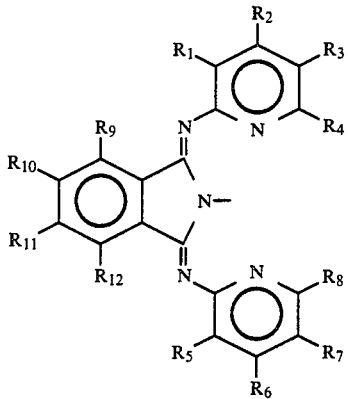

in which n=1 or 2, p=0 or 1 and n+p=2, both ligands L being either identical or different when n=2, $R_1$ to $R_{12}$, identical or different, are a hydrogen atom, an alkyl group, an aryl group, an aralkyl group, an alkoxy group, an alkoxy-alkyl group, a halogen atom, a nitro group, or two adjacent groups $R_1$ to $R_{12}$ form an aromatic ring together with the carbon atoms to which they are linked, X is an acetate, a propionate, a benzoate, a pivalate, a stearate, a 2-ethyl-hexanoate, an octoate, a napthenate, trifluoroacetate, or a hydroxide, M is cobalt, manganese, iron or copper and Y is a peroxo group or a group of formula OOR wherein R is alkyl or aralkyl group.

2. A complex according to claim 1, wherein M is iron or cobalt Y is a group of formula OOR wherein R is a tertiary alkyl or tertiary aralkyl group.

3. A complex according to claim 1, wherein each of $R_1$ to $R_{12}$, in ligand L, is a hydrogen atom.

4. A complex according to claim 1, wherein $R_2$ and $R_6$ simultaneously represent a methyl or tert-butyl group, $R_{11}$ is a methyl or tert-butyl group, $R_1$, $R_3$, $R_4$, $R_5$, $R_7$–$R_{10}$ and $R_{12}$ each represent a hydrogen atom.

5. A complex according to claim 1, wherein M is cobalt and n=p=1.

6. A complex of claim 1, wherein Y is —OOR and M is cobalt.

7. A complex of claim 1, wherein the complex is (BpI)Co(OAc)OOtBu, (BpI)Co(OBz)OOtBu, (BpI)Co(p-NO$_2$BzO)OOtBu, (4'Me-BpI)Co(OAc)OOtBu, (4'Me-BpI)Co(OBz)OOtBu, (5'tBu-BpI)Co(OAc)OOtBu, (5tBu-BpI)Co(OBz)OOtBu, (5'Cl-BpI)Co(OAc)OOtBu, (BpI)CO(octoate)OOtBu, (BpI)Co(OAc)OO cumyl, (BpI)Co(OBz)OO cumyl, (BpI)Fe(OAc)OOtBu, (BpI)$_2$Fe(OOtBu), (BpI)Mn(OAc)OOtBu, (BpI)Mn(OBz)OOtBu,(BpI)$_2$MnOOtBu or (4'Me-BpI)$_2$MnOOtBu, wherein (BpI) is 1,3-bis(2'-pyridylimino) isoindolyl, OAc is an acetate group, OBz is a benzoate group, pNO$_2$BzO is a p-nitrobenzoate group, Me is a methyl group and tBu is a tert-butyl group.

8. A complex of claim 1, wherein two adjacent groups $R_1$ to $R_{12}$ form an aromatic ring together with the carbon atoms to which they are linked.

* * * * *